US006319518B1

(12) United States Patent
Lee et al.

(10) Patent No.: US 6,319,518 B1
(45) Date of Patent: *Nov. 20, 2001

(54) COLON SELECTIVE DRUG DELIVERY COMPOSITION

(75) Inventors: Seung-Seo Lee; Sung-Bum La; Chang-Baeg Lim; Sujung Lee; Bo-Youn Seo; Chaul-Min Pai, all of Taejeon (KR)

(73) Assignee: Samyang Corporation (KR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/919,957

(22) Filed: Aug. 29, 1997

(30) Foreign Application Priority Data

Jul. 3, 1997 (KR) ................................... 97-30767

(51) Int. Cl.⁷ ............................... A61K 9/22; A61K 9/26; A61K 9/36; A61K 9/64
(52) U.S. Cl. ......................... 424/468; 424/469; 424/478; 424/479; 424/964; 424/965; 424/460; 424/451
(58) Field of Search .................... 424/464, 451, 424/456, 460, 461, 468, 469, 478, 479, 964, 965

(56) References Cited

U.S. PATENT DOCUMENTS 5,525,634  6/1996  Sintov et al. ........................ 514/771

FOREIGN PATENT DOCUMENTS

WO0732  of 0000  (WO).

OTHER PUBLICATIONS

Peker–Basara et al, Properties of gelatin–gum arabic coacervates composited with amino resins; AN 1993:103259 see abstract (CAPLUS).*
European Search Report, Nov. 13, 1998.
XP–002082251, international journal of pharmaceutics 126 (1995) 161–168.

* cited by examiner

Primary Examiner—Theodore J. Criares
(74) Attorney, Agent, or Firm—Anderson Kill & Olick

(57) ABSTRACT

A composition comprising gelatin and a polysaccharide which is degradable by a colonic enzyme and, optionally, with an aldehyde and/or a polyvalent metal ion and/or an additional polysaccharide, which is not degraded or disintegrated in the upper gastrointestinal tract, thereby rendering the active substance loaded therein to be selectively delivered to the colon and to be effectively released in the colon.

13 Claims, 4 Drawing Sheets

COLON SELECTIVE DRUG DELIVERY COMPOSITION

FIELD OF THE INVENTION

The present invention relates to a composition for delivering a drug selectively to the colon. Specifically, the present invention relates to a colon selective drug delivery composition comprising gelatin and a polysaccharide which is degradable by colonic enzymes, and optionally an aldehyde and/or a polyvalent metal ion and/or a colon degradable, additional polysaccharide.

BACKGROUND OF THE INVENTION

A system for selectively delivering a drug to colon by an oral administration (hereinafter "colon selective drug delivery system") has several pharmaceutical benefits. First, the colon selective drug delivery system allows local treatment of a colonic disease, e.g., ulcerative colitis, Crohn's disease or colon cancer. Second, the colon selective drug delivery system allows lowering of the dose of a drug because the drug can directly act on the colon, thus reducing undesirable and potentially harmful side effects compared with a systemic administration.

Further, the colon selective drug delivery system is useful in administering a drug which is an irritant to the mucosa of the upper gastrointestinal tract such as the stomach or small intestine, e.g., non-steroidal anti-inflammatory agents; or a drug which is degraded by gastric juice or an enzyme present in the upper gastrointestinal tract, e.g., a peptide or protein. It was reported that the preferred targeting site of protein drugs is the colon because the concentration of a protease is significantly lower in the colon than in the stomach or small intestine (see J. Kopecek et al., *Proc. Int. Symp. Control. Rel. Bioact. Material* 17, 130–131, 1990).

Further, it was recently reported that the colon selective drug delivery system delays the efficacy of drug for a long time and increase the bioavailability of the drug (see A. Sintov et al., *Int. J. Pharma.*, 143, 101–106, 1996). That is, in case of the colon selective drug delivery system, the drug resides at the colon for a longer time than at other digestion organs, and therefore, the time for drug absorption becomes prolonged and the total bioavailability of the drug increases.

A composition for selectively delivering a drug to the colon generally must meet the following four requirements: (1) the composition is not degraded or disintegrated at the upper gastrointestinal tract; (2) the composition does not release the drug loaded therein at the upper gastrointestinal tract; (3) the composition releases the drug effectively at the targeting site of the colon, e.g., the ascending colon, the transverse colon or the descending colon; and (4) the composition is easy to formulate in a form suitable for loading the drug. Further, it is preferred that the composition has a good processability.

Many studies have been made to develop such a colon selective drug delivery composition satisfying the above requirements. For example, U.S. Pat. Nos. 5,482,718; 4,627,851; 4,693,895; 4,705,515; and 4,904,474; EP 621 032 A1; JP 34929/1991 A; U.S. Pat. No. 5,536,507; EP 453 001 A1; U.S. Pat. No. 5,171,580; and EP 572 942 A2 disclose time-controlled drug compositions which are designed to prevent the drug release for a period which is expected to be sufficient for the composition to pass through the upper gastrointestinal tract. Further, U.S. Pat. Nos. 5,401,512 and 5,541,170 and WO 95/11024 describe drug compositions for selectively releasing the drug in the colon by way of exploiting the difference in pH between the colon and other digestion organs.

However, the above-mentioned compositions are not always effective in delivering the drug to the colon because the transit time and the pH in the upper gastrointestinal tract vary among individuals.

Further, there was reported a prodrug which is prepared by covalently bonding drug molecules to carrier molecules wherein the covalent bond is broken only by an enzyme produced by colonic bacteria, in order that the prodrug is degraded to release the drug only at the colon (see WO 84/04041 and WO 93/22334; A. D. McLeod et al., *J. Pharm. Sci.* 83, 1284–1288, 1994; D. R. Friend et al., *J. Med. Chem.* 27, 261–266, 1984; B. Haeberlin et al., *Pharm. Res.* 10, 1553–1562, 1993; D. R. Friend et al., *J. Med. Chem.* 28, 51–57, 1985; D. R. Friend, *S.T.P. Pharma Sci.* 5, 70–76, 1995; and J. P. Brown et al., *J. Med. Chem.* 26, 1300–1307, 1983).

However, in order to use a drug in the form of a prodrug, the drug must meet the requirements that it has at least one functional group for said covalent bonding; it is stable enough to endure the condition of a covalent bond forming reaction and the prodrug can easily revert to the drug in the colon. Due to the above limitations, it is very hard to develop a prodrug.

It is well known that enzymes capable of breaking an azo bond or various bonds in a polysaccharide are present in the colon. WO 91/16057 and EP 398 472 A2 disclose compositions containing an azo polymer having azo bonds. This technique exploits the fact that azo bonds are not degraded at the upper gastrointestinal tract, but degraded at the colon. This method has an advantage in that the composition is relatively stable at the upper gastrointestinal tract. However, it was reported that azo reductase cannot easily approach the azo bond of the azo-polymer due to the hydrophobic nature of the azo-polymer, thus resulting in slow degradation of the composition containing the azo polymer at the colon (see P. Y. Yeh et al., *Macromol. Chem. Phys.*, 196, 2183–2202, 1995). Therefore, the composition containing the azo polymer has the critical disadvantage that release of the drug from the composition is not effective in the colon. And, a composition containing an azo polymer has a problem of safety as well.

The technique of using enzymes capable of breaking various bonds in polysaccharides are more beneficial than that of using the azo bond breaking enzyme, in terms of safety and degradability at the colon; for the most part, polysaccharides are natural polymers which are safe, biodegradable, and hydrophilic.

For example, U.S. Pat. No. 4,432,966 discloses a composition comprising microcrystalline cellulose and ethyl cellulose; EP 627 173 A1 describes a cellulose composition; WO 95/35100 discloses a starch capsule and a composition comprising an enteric coating; U.S. Pat. No. 5,422,121 suggests a composition containing a guar gum or locust bean gum blended with ethyl cellulose. However, it is difficult to form a polysaccharide film, and therefore, a polysaccharide is generally formulated together with a hydrophobic film forming material. A hydrophobic film forming material generally has a lower swelling ratio than that of a polysaccharide. Due to this difference in the swelling ratio, the film made of a polysaccharide and a film forming material may crack during the passage through the stomach and small intestine. Accordingly, in this method, the drug is released at the upper gastrointestinal tract.

On the other hand, WO 94/01136 discloses a delivery composition containing a chemically cross-linked hydrogel of dextran. However, this composition also has problems:

the hydrogel swells during its passage through the upper gastrointestinal tract, releasing a major portion of the drug loaded in the composition; and when the composition reaches the colon, the composition is very slowly degraded due to the presence of strong cross-linking chemical bonds, thus rendering the drug delivery not colon selective.

Further, U.S. Pat. No. 5,505,966 discloses a pharmaceutical composition containing calcium pectinate as a major component and a filler such as pectin, dextran and/or avicel. U.S. Pat. No. 5,525,634 describes a pharmaceutical composition containing a synthetic or natural polymer which is degradable by a colonic enzyme, wherein calcium pectinate is disclosed as an example of a natural polymer.

In the '966 patent, the calcium pectinate composition is employed in the form of a coacervate pellet, but it has the disadvantage that calcium pectinate, which is insoluble in water, converts to a water soluble sodium or potassium pectinate in the course of passing through the upper gastrointestinal tract by exchanging calcium ions with sodium ions or potassium ions present in the digesting solution, and therefore, the pellets disintegrate and release the drug therefrom.

To solve the above problem, the '634 patent suggests a compressed tablet formulation which is prepared by pulverizing and compressing a pharmaceutical composition containing a drug and calcium pectinate. However, this method has various problems that the composition is difficult to pulverize and the tablet disintegrates easily in the upper gastrointestinal tract due to the high swelling property of calcium pectinate. Therefore, the compositions disclosed in both the '966 and the '634 patents depend considerably on swelling, thus on the transit time through the upper gastrointestinal tract, and not on unique characteristics of the composition.

SUMMARY OF THE INVENTION

It is, therefore, an object of the present invention to provide a colon selective drug delivery composition which satisfies the above-mentioned four requirements.

Further, it is an object of the present invention to provide a pharmaceutical composition comprising the inventive colon selective drug delivery composition.

In accordance with an aspect of the present invention, there is provided a colon selective drug delivery composition comprising gelatin and a polysaccharide which is degradable by colonic enzymes; and, optionally, an aldehyde and/or a polyvalent metal ion and/or a colon degradable additional polysaccharide.

In accordance with another aspect of the present invention, there is provided a colon selective pharmaceutical composition or formulation comprising the inventive colon selective drug delivery composition and a biologically active substance.

BRIEF DESCRIPTION OF DRAWINGS

The above and other objects and features of the present invention will become apparent from the following description, taken in conjunction with the accompanying drawings, wherein.

DETAILED DESCRIPTION OF THE INVENTION

Figure 1:
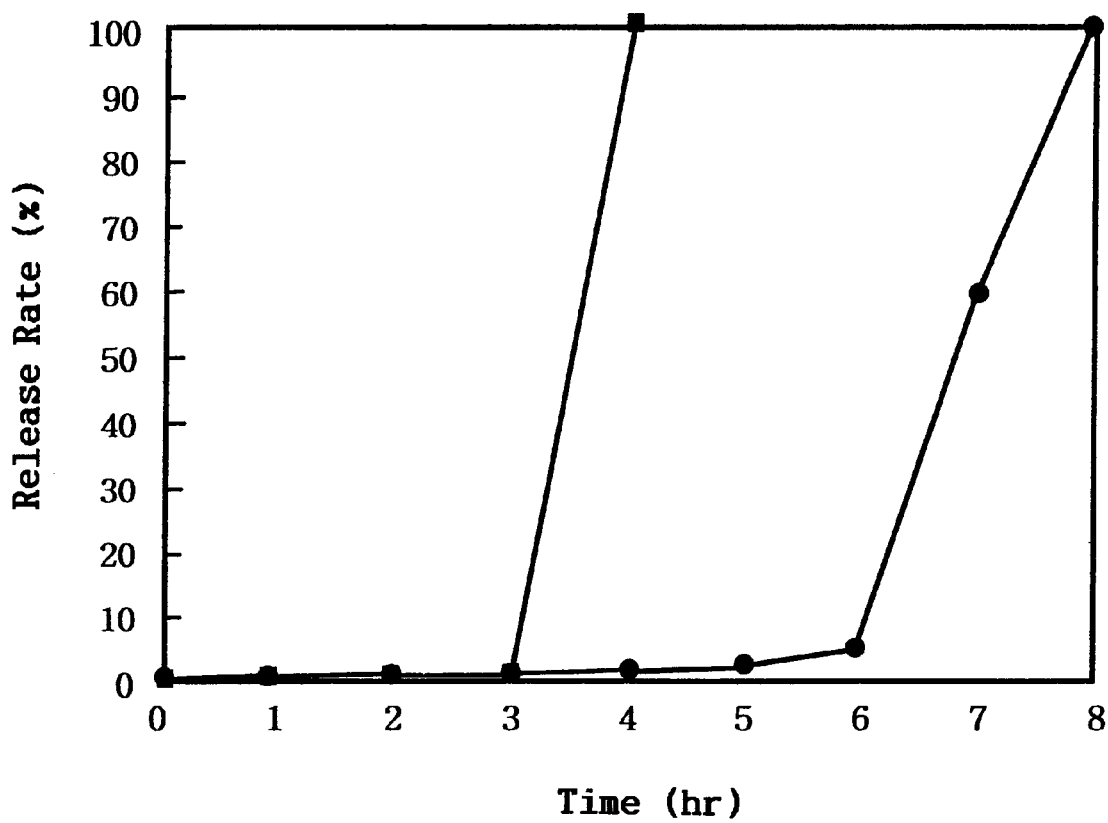
FIG. 1 shows the result of in vitro drug release tests conducted for a prednisolone tablet coated with a pectinate/gelatin film prepared in accordance with the present invention, and for a prednisolone tablet coated with a calcium pectinate film.

As described previously, calcium pectinate which has been employed in the prior art readily converts to a water soluble sodium or potassium pectinate in the digestive fluid of the upper gastrointestinal tract, thereby rendering a pharmaceutical composition containing calcium pectinate susceptible to premature release of the drug loaded therein before the composition reaches the colon.

To solve this problem, the present invention provides a composition comprising gelatin and a polysaccharide to enhance the strength of the composition. Gelatin employed in the drug delivery composition in accordance with the present invention forms a complex with a polysaccharide by complicated intermolecular forces including ionic bonding, hydrogen bonding, steric forces and so on, thus providing a composition with a mechanical strength higher than that of calcium pectinate.

Although gelatin itself may be degraded by a protease present in the upper gastrointestinal tract, the complex of gelatin with the polysaccharide according to the present invention is hardly degraded in the upper gastrointestinal tract, as demonstrated in Example 6. This is considered to be due to the fact that the chains of the polysaccharide molecules penetrate into the chains of gelatin molecules and inhibit access of protease to the gelatin chains.

Therefore, when the delivery composition of the present invention is loaded with a drug as an active substance, the drug release in the upper gastrointestinal tract can be prevented, rendering the drug colon selective.

Further, in case of a composition comprising a chemically modified polysaccharide or the hydrophobic polymer in the prior art, the composition frequently would not effectively release the drug even in the colon. The composition of the present invention comprising an unmodified hydrophilic pectinate/gelatin, however, can release the active substance effectively in the colon because the hydrophilic polysaccharide which is not chemically modified can be easily degraded by colonic enzymes in the colon. Furthermore, the gelatin complex can be degraded by a small but significant amount of protease present in the colon, thus providing a synergistic effect on the degradation of the polysaccharide by a colonic enzyme. Accordingly, the inventive drug delivery composition enables a rapid release of the active substance in the colon.

In the inventive drug delivery composition, gelatin may be employed in an amount ranging from 0.01 to 99.99% by weight, preferably 1 to 99% by weight of the composition.

The polysaccharide of the present invention may be an acidic or an anionic polysaccharide and representative examples thereof may include pectinate, pectate, alginate, chondroitin sulfate, polygalacturonic acid, tragacanth gum, arabic gum, and a mixture thereof. The polysaccharide may be employed in an amount ranging from 0.01 to 99.99% by weight, preferably 1 to 99% by weight of the composition.

A colonic disease such as ulcerative colitis and Crohn's disease may occur at various sites on the colon. The composition of the present invention comprising gelatin and the polysaccharide may release all of the active substance at the ascending colon and, therefore, may not deliver the active substance to the downstream region of the colon. In order to retard the active substance release, the composition may further comprise an additional component to provide the composition with a semi-interpenetrating polymer network or an interpenetrating polymer network, thus controlling the targeting site in the colon.

As the additional component, the composition of the present invention may comprise an aldehyde which can crosslink gelatin. Representative examples of the aldehyde may include formaldehyde, gluteraldehyde, terpene, cinnamaldehyde, aldose, and a mixture thereof. The aldehyde must be employed in the present invention in an amount less than 1% by weight.

The aldehyde used in the present invention reacts with an amino group of gelatin, not with a hydroxyl group of the polysaccharide, to form a semi-interpenetrating polymer network (SIPN) structure into which the polysaccharide molecules penetrate. The SIPN structure retards disintegration of the crosslinked gelatin but easily breaks down once the polysaccharide begins to be degraded. Thus, a colon selective drug delivery composition comprising an aldehyde crosslinked gelatin penetrated by non-crosslinked polysaccharide is suitable for delivering the active substance to a deep site in the colon.

The composition of the present invention may further comprise a polyvalent metal ion. Representative examples of the polyvalent metal ion include calcium, magnesium, strontium, barium, ferrous or ferric, zinc, aluminum, bismuth and zirconium ions, and a mixture thereof. Preferred polyvalent metal ion is a calcium ion. The polyvalent metal ion may be employed in an amount ranging from 0.0001 to 50% by weight, preferably 0.0001 to 20% by weight of the composition.

The polyvalent metal ion may be reacted with the carboxylic group of the polysaccharide as a role of crosslinking agent to form a polymer network. In case the polyvalent metal ion is incorporated with the molecules of the polysaccharide penetrating into the network of gelatin, the polysaccharide molecules are crosslinked with the polyvalent metal ion to form another network, the two polymer networks being interpenetrated, not crosslinked. The interpenetrating polymer network (IPN) structure thus produced has a higher mechanical strength than that of the SIPN formed by the addition of the aldehyde compound alone, and therefore, is not easily disintegrated at the start site of the colon and has a longer lag time than that of the SIPN structure. Accordingly, the colon selective drug delivery composition comprising a gelatin, a polysaccharide, an aldehyde and a polyvalent metal ion is suitable for delivering the active substance loaded therein to a deeper site in the colon.

The composition of the present invention may further comprise an additional colon-degradable polysaccharide which does not form a complex with gelatin and is degradable by colonic enzymes. When the additional polysaccharide is incorporated with the SIPN or IPN structure of the present invention, it forms another polymer chain which is not crosslinked with, but penetrates into the network, thus increasing the mechanical strength of the composition by strengthened hydrogen bonding and other intermolecular forces. In addition, the additional polysaccharide contained in the composition can function as another barrier to drug diffusion and render the composition unable to release the drug in the upper gastrointestinal tract. However, the composition is easily degraded in the colon because the additional polysaccharide is easily degraded by the colonic enzymes present in the colon and functions to shorten the lag time of the active substance in the colon, contrary to the function of an aldehyde and a polyvalent metal ion.

The additional polysaccharide may be neutral and representative examples thereof may includes dextran, amylose, arabinogalactan, arabinoxylan, cellulose, guar gum, laminarin, locust bean gum, pectin, starch, xylan, or a mixture thereof. The preferred additional polysaccharide is dextran. The additional polysaccharide may be employed in an amount ranging from 0.0001 to 45% by weight of the composition.

The delivery composition of the present invention may further comprise a pharmaceutically acceptable additive. Examples of such an additive may include a plasticizer, a pigment, a sweetening agent and the like. Representative examples of the plasticizer which may be employed to facilitate the formulation of the composition may include glycerin, triacetin, sorbitol, polyethylene glycol, propylene glycol, citrate, phthalate, castor oil and the like. The preferred plasticizers are glycerin, triacetin and sorbitol. The plasticizer may be employed in an amount ranging from 0.1 to 100 parts by weight, preferably 35 to 100 parts by weight, per a part by weight of the total polymeric components (dry weight basis) in the composition.

With the composition containing gelatin and a polysaccharide, and, optionally, an aldehyde and/or a polyvalent metal ion and/or an additional polysaccharide, as described above, in accordance with the present invention, various pharmaceutical formulations including coated tablets, capsules, pills and so on may be easily manufactured, and an active substance is easily loaded in the formulation. Therefore, the colon selective drug delivery composition of the present invention satisfies all the conditions required for a composition for selectively delivering a drug to the colon: (1) the composition is not degraded or disintegrated at the upper gastrointestinal tract; (2) the composition does not release the drug loaded therein at the upper gastrointestinal tract; (3) the composition releases the drug effectively at the targeting site of the colon; and (4) the composition is easy to formulate in a form suitable for loading the drug. Further, the delivery composition of the present invention also has a good processing property.

The present invention also provides a colon selective pharmaceutical composition comprising a biologically active substance and the inventive colon selective drug delivery composition as mentioned above.

Representative examples of the active substance which may be employed in the pharmaceutical composition of the present invention may include topical active drugs for the treatment of colon diseases, e.g., ulcerative colitis, Crohn's disease, hypersensitive colon symptom, colon cancer and constipation. Specifically, the active substance may include mesalazine, sulfasalazine, ibuprofen, prednisolone, dexamethasone, budesonide, beclomethasone, flucticasone, thioxocortal, hydrocortisone, cyclosporins, methotrexate, domperidone, 5-fluorouracil, bisacodyl, a dietary fiber, bifidobacteria and a mixture thereof. Further, the active substance may include a systemic active drug such as peptide or protein, or an agent for the treatment of asthma, rheumatism, arthritis, calcium antagonist and the like; specifically, insulin, vasopressin, a growth hormone, a growth factor, a colony stimulating factor, calcitonin, immunoglobulins, diltiazem, verapamil, nifedipin, captopril, theophylline, naproxen and a mixture thereof. Also, the pharmaceutical composition of the present invention may include diagnostic reagents and nutrients as active substances. The active substance which may be used in the pharmaceutical composition of the present invention is not limited to those mentioned above.

The pharmaceutical composition of the present invention may be prepared by inserting a biologically active substance into a capsule made of the inventive delivery composition, or by coating any known pharmaceutical formulation with the inventive drug delivery composition. The pharmaceutical composition may be in the form of a capsule, a coated tablet, a coated pill, a coated seed, or a coated capsule.

When the delivery composition of the present invention is coated on a known pharmaceutical formulation, the coating process may be conveniently conducted by spraying the colon selective drug delivery composition of the present invention. The coating amount of the delivery composition of the present invention may range from 1 to 100 mg/cm$^2$, preferably from 20 to 50 mg/cm$^2$, of the surface area of the formulation.

In a preferred embodiment, the inventive delivery composition to be coated on a known pharmaceutical formulation may contain 0.1 to 99.9%, preferably 5 to 50% by weight, of gelatin and 0.1 to 99.9%, preferably 50 to 95% by weight, of a pectinate and, optionally, 0 to 99.9%, preferably 0 to 45% by weight of dextran on the basis of the weight of the composition. The delivery composition may further comprise a plasticizer in an amount ranging from 10 to 100% by weight based on the weight of the polymeric components.

The aldehyde and/or polyvalent metal ion which may be employed in the present invention as an additional component, may be applied on a pharmaceutical formulation coated with a coating composition containing no such additional components. The additional components may be applied by dipping the previously coated formulation into a solution containing the aldehyde and/or the polyvalent metal ion. Formaldehyde and gluteraldehyde are preferred for such an application and they may be employed in the form of 0.01 to 50 wt %, preferably 0.01 to 20 wt %, of an alcohol solution. The dipping process of the aldehyde compound may be carried out with stirring for a period ranging from 1 second to 60 minutes, preferably from 1 to 30 min. The polyvalent metal ion, which is employed to cross-link the polysaccharide, may be used in the form of an aqueous solution having a concentration of 0.01 to 99.9 wt %, preferably 0.1 to 30 wt %, and the dipping process thereof may be conducted for a period ranging from 1 min. to 72 hrs, preferably from 10 min. to 2 hrs.

Although the coated formulation is preferably dried by drying slowly at a relative humidity of less than 20% for 48 hours or longer, other drying procedures may also be used.

Alternatively, the aldehyde and/or polyvalent metal ion may be employed directly in the composition to be coated on the formulation. The aldehyde which may be employed directly in the coating composition is preferably terpene, cinnamaldehyde, or aldose.

Besides a coated capsule formulation, a capsule formulation may be prepared by shaping the drug delivery composition of the present invention into a capsule and filling a biologically active substance into the capsule. The capsule may be a hard or soft capsule and may be prepared by using a pin molder or a rotary die. The capsule formulation has the advantage that more drugs having widely varying properties can be formulated than possible with other forms of formulation.

In another embodiment, a soft capsule may be prepared using the delivery composition of the present invention by exploiting the phenomenon that the sol-gel transition of gelatin occurs at a temperature ranging from 40 to 50° C. An example of a composition for the production of a soft capsule is one containing 0.1 to 99.9%, preferably 50 to 99.9%, by weight of gelatin and 0.1 to 99.9%, preferably 0.1 to 50%, by weight of pectinate and, optionally, 0 to 45% by weight of dextran. Preferably, the soft capsule composition contains an excess amount of gelatin sufficient to induce the gel-sol phase change which facilitates the processing step for the preparation, e.g., a rotary die. Further, the inventive soft capsule composition may contain a plasticizer in an amount of 5 to 100% by weight based on the total weight of the polymeric components in the composition.

A biologically active substance may be filled into a capsule in the form of an oily dispersion, powder, granules or pellets.

The pharmaceutical composition of the present invention is not limited to the above mentioned embodiments and modification and change may be made thereto by a person skilled in the art.

The following examples are only provided for the purposes of illustrating certain aspects of the present invention; they are not to be construed sa limiting the scope of the present invention in any way.

EXAMPLE 1

Preparation of colon selective film composition CSC-1

Pectin (USP/200, Copenhagen Pectin, Denmark) was dissolved in water and the pH was adjusted to 7 by adding sodium carbonate and sodium chloride, followed by adding water thereto to obtain a 10 wt % pectin solutions. Gelatin (Kyungki Gelatin, Korea) was then added to the above solution in an amount of 20 wt % based on the dry weight of pectin, and the resulting solution was homogenized at 50° C. Glycerol was added thereto in an amount of 80 wt % based on the combined amount of pectin and gelatin. The resulting mixture was homogenized at 50° C. and cast into a film having a thickness of 0.1 mm on a silicone plate by using a casting blade. The film was then air-dried by 48 hours to obtain a gelatin/pectinate film, which was designated CSC-1.

EXAMPLE 2

Preparation of colon selective film composition CSC-2

CSC-1 obtained in Example 1 was immersed in an ethanol solution containing 3 wt % formaldehyde for 3 min., air-dried for 48 hours and cut into 1 cm×1 cm pieces. This aldehyde crosslinked gelatin/pectinate film was designated CSC-2.

EXAMPLE 3

Preparation of colon selective film composition CSC-3

CSC-2 prepared in Example 2 was soaked in a 10 wt % CaCl$_2$ solution for 2 hours, washed with distilled water, air-dried and cut to obtain 1 cm×1 cm pieces of an aldehyde-crosslinked gelatin/calcium pectinate film, which was designated CSC-3.

EXAMPLE 4

Preparation of colon selective film composition CSC-4

A 10 wt % pectin solution was prepared as in Example 1 and dextran (Sigma, molecular weight=5,000 kDa) was added thereto in an amount of 12.5 wt % based on the dry weight of pectin. Introduced to the resulting solution was gelatin in an amount of 20 wt % based on the amount of pectin, and then, glycerol was added thereto in an amount of 80 wt % based on the combined amount of pectin, dextran and gelatin. The solution thus obtained was homogenized and cast into a film by the procedure of Example 1. The film was cut into 1 cm×1 cm pieces, which were immersed in a 3 wt % formaldehyde ethanol solution for 3 min.; air-dried; soaked in a 10% CaCl$_2$; washed with distilled water; and air-dried for 48 hours. The aldehyde-crosslinked gelatin/calcium pectinate/dextran film thus obtained was named CSC-4.

Comparative Example 1

Preparation of calcium pectinate film

A calcium pentinate film was prepared by the procedure of Example 1 except that the use of gelatin was omitted and the prepared pectinate film was soaked in 10 wt % CaCl$_2$ aqueous solution, washed and dried.

Comparative Example 2

Preparation of gelatin film

An aqueous solution containing 43 wt % gelatin and 17 wt % glycerol was homogenized at 60° C. and cast into a film as in Example 1. The gelatin film thus obtained was cut into 1 cm×1 cm pieces which were immersed in a 3 wt % formaldehyde ethanol solution for 3 min. and air-dried.

EXAMPLE 5

Properties of colon selective films: dissolution test

The colon selective film prepared in Example 1, CSC-1, and the calcium pectinate film prepared in Comparative Example 1 were subjected to dissolution tests using the dissolution solution cited in US Pharmacopoeia (USP) 23 to evaluate their stabilities under simulated pH and ionic environments of the stomach and the small intestine. For this purpose, a 1 cm×1 cm sample piece was accurately weighed and treated at 37° C., stirred in Solution 1 (pH 1.2) for 2 hours, dried and weighed. Subsequently, the sample pieces was placed in Solution 2 (pH 6.8), stirred for 6 hours at 37° C., dried and weighed. Three such measurements were conducted for each sample and the averaged values are shown in Table 1.

The result clearly demonstrates that the colon selective film composition of the present invention is much more resistant to an ionic exchange under simulated upper gastroenteric pH and ionic conditions than the conventional calcium pectinate film.

TABLE 1

|  | Weight loss in Solution 1, wt % | Weight loss in Solution 2, wt % |
|---|---|---|
| CSC-1 | 2 | 10 |
| Calcium pectinate | 4 | 62 |

EXAMPLE 6

Properties of colon selective film compositions: Disintegration test

Each of the colon selective film compositions prepared in Examples 1–4 and the gelatin film prepared in Comparative Example 2 were subjected to a disintegration test as follows.

A sample was weighed and subjected to the following successive extractive treatment steps at 37° C. using a constant-temperature shaker operated at 100 rpm, and the dried sample was weighed after each step:

(step 1) 2 hours in a simulated gastric fluid (pH 1.2);

(step 2) 4 hours in a simulated intestinal fluid (pH 7.5); and (step 3) 4 hours in a simulated colonic fluid, wherein:

the simulated gastric fluid was prepared by dissolving 2.0 g of sodium chloride, 3.2 g of pepsin and 7.0 ml of conc. HCl in distilled water to obtain a solution having a total volume of 1 liter; the simulated intestinal fluid was prepared by adding 190 ml of 0.2 N NaOH, 400 ml of distilled water and 10 g of pancreatin to an aqueous potassium hydrogen phosphate solution, adjusting the pH of the resulting solution to 7.5 and adding distilled water to obtain a solution having a total volume of 1 liter; and the simulated colonic fluid was prepared by substituting Pectinex Ultra SP-L (Novo Nordick, Switzerland) for pancreatin in the above simulated intestinal fluid preparation.

The results of such measurements are summarized in Table 2.

TABLE 2

Film Sample weight after each of the simulated gastric, intestinal and colonic fluid treatment steps, wt % of the original weight.

|  | Gastric | Intestinal | Colonic |
|---|---|---|---|
| Gelatin film | 89 | 0 | 0 |
| CSC-1 | 98 | 83 | 0 |
| CSC-2 | 98 | 89 | 34 |
| CSC-3 | 98 | 95 | 58 |
| CSC-4 | 98 | 96 | 40 |

The data in Table 2 show that the gelatin film prepared in Comparative Example 2 undergoes complete disintegration in the simulated intestinal fluid, while the colon selective film compositions prepared in Examples 1–4, i.e., CSC-1, 2, 3, and 4 are stable in the intestinal fluid and undergo significant disintegration only in the simulated colonic fluid. It may be noted that CSC-1, which is a pectin-gelatin composition having no cross-linking in either the pectin or the gelatin component, easily disintegrates in the simulated colonic fluid, whereas the pectin-gelatin compositions, CSC-2, 3 and 4, each having a different mode of cross-linking, undergo limited disintegration in the colonic fluid.

EXAMPLE 7

Preparation of a coated tablet composition

Pectin (USP/200, Copenhagen Pectin, Denmark) was dissolved in distilled water, the pH of the resulting solution was adjusted to 7 by adding sodium carbonate and sodium chloride an the resulting solution was diluted with distilled water to obtain a 5 wt % pectin solution. Gelatin was added thereto in an amount of 20 wt % based on the dry weight of pectin, the mixture was homogenized at 50° C., glycerol was added thereto in an amount of 80 wt % based on the combined amount of pectin and gelatin, and then the resulting mixture was homogenized.

The above solution was employed in costing prednisolone tablets (each containing 10 mg of the active ingredient) using Hi-Coater (Freund Ind., Japan) under the conditions of inlet temperature=75° C., outlet temperature=38° C., spray air pressure=0.2 MPa, coating solution supply rate=1.4 ml/min. and fan velocity=12 rpm.

EXAMPLE 8

Preparation of colon selective coated tablet, CSCT-1

The coated tablets prepared in Example 7 were immersed in a 3 wt % formaldehyde in ethanol for 3 minutes, washed with ethanol and dried in a desiccator for 48 hours to obtain prednisolone tablets coated with an aldehyde-crosslinked gelatin/pectin composition. This colon selective tablet composition is designated as CSCT-1.

EXAMPLE 9

Preparation of colon selective tablet, CSCT-2

The colon selective tablet CSCT-1 obtained in Example 8 was soaked in a 10 wt % $CaCl_2$ solution for 2 hours, washed with distilled water and dried in a desiccator for 48 hours to obtain prednisolone tablets coated with an aldehyde-crosslinked gelatin/calcium pectinate composition. This colon selective tablet composition was named CSCT-2.

EXAMPLE 10

Preparation of colon selective tablet, CSCT-3

A 5 wt % pectin solution was made as in Example 7 and dextran (Sigma, MW=5,000 kDa) was added thereto in an amount of 12.5 wt % based on the amount of pectin. Added to the resulting mixture was gelatin in an amount of 5 wt % based on the amount of pectin, and the resulting mixture was homogenized to obtain a coating solution.

Prednisolone tablets each containing 10 mg of the active ingredient were coated using the above coating solution with Hi-Coater under the conditions described in Example 7. The amount of the coating material on the coated tablets thus obtained was estimated at 26 mg/cm$^2$.

The coated tablets obtained above were immersed in an ethanol solution containing 3 wt % formaldehyde for 3 minutes, dried, soaked in a 10 wt % $CaCl_2$ solution for 2 hours, washed with distilled water, and air-dried for 48 hours to obtain prednisolone tablets coated with an aldehyde-crosslinked gelatin/calcium pectinate/dextran composition. This colon selective tablet composition is designated as CSCT-3.

Comparative Example 3

Preparation of tablets coated with calcium pectinate

Prednisolone tablets (each containing 6 mg of the active ingredient) were coated with a pectinate by the procedure of Example 7 except for the use of gelatin. The pectin-coated tablets were treated with $CaCl_2$ as in Example 9 to obtain prednisolone tablets coated with calcium pectinate. The amount of calcium pectinate coating was estimated at 26 mg/cm$^2$.

EXAMPLE 11

In vitro drug release test

The coated prednisolone tablets prepared in Example 7 and Comparative Example 3 were subjected to in vitro drug release tests employing a dissolution tester. Test solutions were prepared in accordance with USP 23; Solution 1 (pH 1.2) and Solution 2 (pH 6.8), plus Solution 3 prepared by adding Pectinex Ultra SP-L to Solution 2.

Each tube of the dissolution tester (Fine Scientific Instruments, Korea) was loaded with a sample tablet and a test solution and maintained at 37° C. under a paddle speed of 100 rpm. The amount of prednisolone leached into Solution 1 or Solution 2 was determined by measuring the absorbance at 260 nm, while the amount released into Solution 3 (prepared by adding Pectinex Ultra SP-L to Solution 2) was analyzed by either extraction followed by HPLC. Such measurements were repeated at least three times for each sample. The averaged amounts of released prednisolone were expressed in the form of wt % based on the original weight and were plotted against time in FIG. 1. In FIG. 1, ♦ represents a prednisolone tablet coated with gelatin/pectinate film prepared in accordance with the present invention, and ■ represents a prednisolone tablet coated with calcium pectinate film.

As can be seen from the results in FIG. 1, the calcium pectinate-coated tablet released most of its active substance during the period of contact with Solution 2. In contrast, the colon selective tablet formulation obtained in Example 7 kept the drug un-released during its contact with solution 1 and 2, but facile drug release took place when the colon selective tablet met solution 3.

Accordingly, the calcium pectinate-coated tablet prepared in Comparative Example 3 is expected to release all of its active ingredient in the upper gastrointestinal tract, and lacks colon selectivity. The tablet coated with a gelatin/pectinate composition prepared in Example 7, on the other hand, is expected to release prednisolone only then the tablet reaches the large intestine, i.e., colon specific.

EXAMPLE 12

In vitro drug release test: Semi-IPN, IPN

Figure 2:
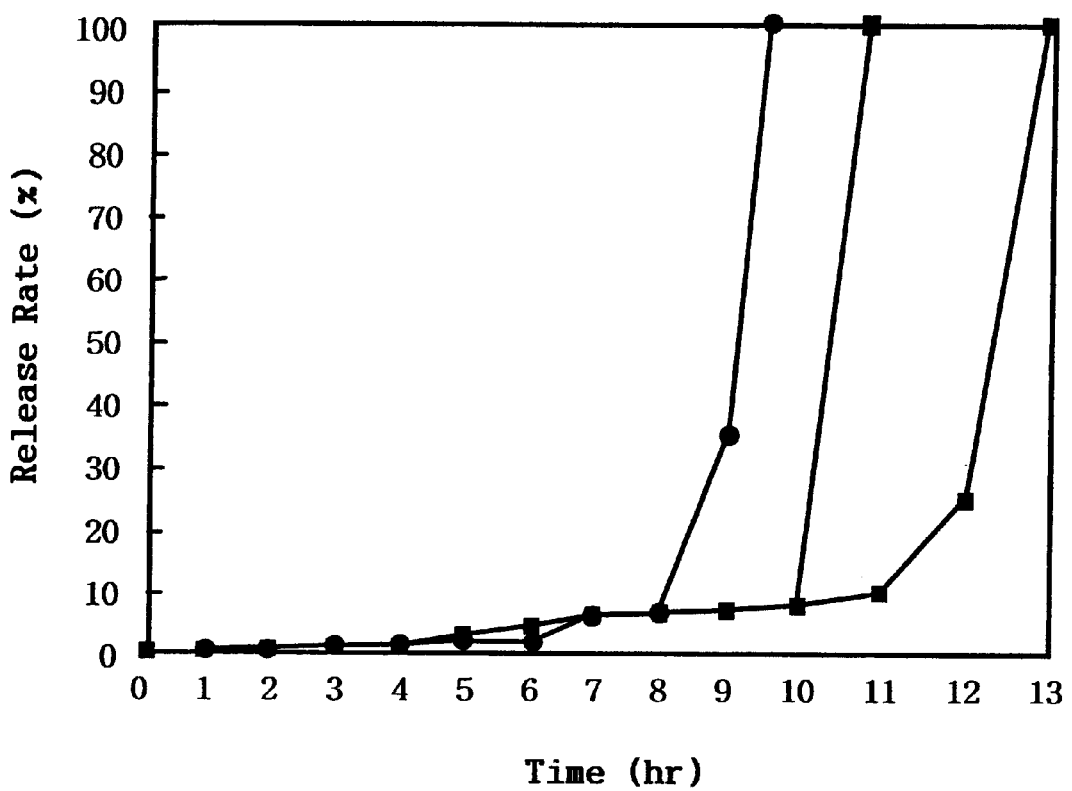
FIG. 2 presents the result of in vitro drug release tests conducted for a prednisolone tablet coated with an aldehyde-crosslinked gelatin/pectinate film, an aldehyde-crosslinked gelatin/calcium pectinate film and an aldehyde-crosslinked gelatin/calcium pectinate/dextran film prepared in accordance with the present invention.

The in vitro drug release modes of the colon selective tablet formulations prepared in Examples 8, 9 and 10, namely CSCT-1, 2 and 3, were measured by the procedure of Example 11 and the results are shown in FIG. 2. In FIG. 2, ♦ represents a prednisolone tablet coated with aldehyde crosslinked gelatin/pectinate film, ■ represents a prednisolone tablet coated with aldehyde crosslinked gelatin/calcium pectinate film and □ represents a prednisolone tablet coated with aldehyde crosslinked gelatin/calcium pectinate/dextran film.

As shown in FIG. 2, all of the colon selective tablets only released prednisolone in Solution 3, as no significant amount of the drug were released in Solution 1 (pH 1.2) or in Solution 2 (pH 6.8). In Solution 3, the rate of drug release was the fastest with CSCT-1 prepared in Example 8, which was followed by CSCT-3 and then by CSCT-2.

EXAMPLE 13

In vitro drug release test: Long-Term Release

In order to demonstrate the colon selectivity of the pectin-gelatin coated tablets prepared in Example 7, three independent dissolution tests were conducted utilizing Solutions 1, 2 and 3 described in Examples 11, respectively. The amount of prednisolone released into each solution was measured hourly for a period of 24 hours using the procedure of Example 11.

Figure 3:
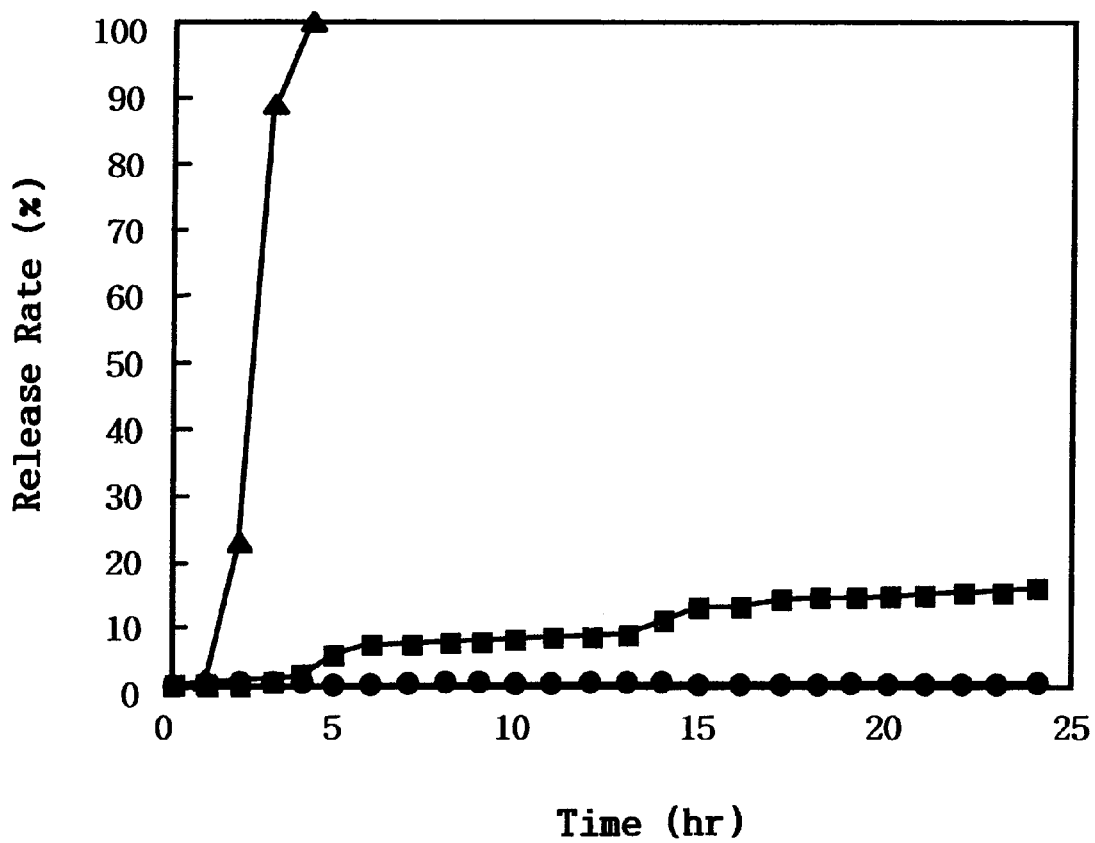
FIG. 3 provides the rates of in vitro drug release by a prednisolone tablet coated with gelatin/pectinate film, prepared in accordance with the present invention, in a simulated gastric fluid, an intestinal fluid and a colonic fluid, respectively.

The results are shown in FIG. 3. In FIG. 3, ♦ represents a simulated gastric fluid, ■ represents a simulated intestinal fluid and represents a simulated colonic fluid. FIG. 3 illustrates the distinction that the drug release is remarkably facile in Solution 3, while it is suppressed in Solutions 1 and 2. The pectinate/gelatin coated tablets prepared in Example 7 was thus confirmed to be colon specific.

EXAMPLE 14

Preparation of soft capsules (1)

An aqueous solution containing 3.08 wt % pectin, 30.15 wt % gelatin and 16.77 wt % glycerol was prepared. Sodium carbonate and sodium chloride were added thereto to obtain a pH 7 solution, and the resulting mixture was homogenized at 60° C. and fed to a rotary die to prepare soft capsules filled with a mineral oil or air. The soft capsules so prepared were dried for 48 hours at a relative humidity of 20%.

EXAMPLE 15

Preparation of soft capsules (2)

The procedure of Example 14 was repeated except that an aqueous solution containing 2.54 wt % pectin, 0.54 wt % dextran (Mw=5,000 kDa), 30.15 wt % gelatin and 16.77 wt % glycerol was used.

EXAMPLE 16

Preparation of soft capsules (Crosslinking (1))

(a) The soft capsules obtained in Examples 14 were treated with an ethanol solution containing 5 wt % formaldehyde for 10 minutes and dried to obtain cross-linked (aldehyde treated) gelatin/pectinate capsules.

(b) The capsules obtained in (a) were soaked in a 10 wt % $CaCl_2$ solution for 2 hours, washed with distilled water and dried for 48 hours at a relative humidity of 20% to obtain soft capsules made of an aldehyde-crosslinked gelatin/calcium pectinate.

EXAMPLE 17

Preparation of soft capsules (Crosslinking (2))

(a) The soft capsules obtained in Example 15 were treated with formaldehyde by the procedure of Example 16a.

(b) The capsules obtained in (a) were treated with calcium chloride by the procedure of Example 16b.

EXAMPLE 18

In vitro disintegration test of soft capsules

The soft capsules obtained in Examples 16 and 17 were subjected to in vitro disintegration tests using the simulated gastric and intestinal fluids described in USP 23 as well as a simulated colonic fluid prepared by adding Pectinex Ultra SP-L to the simulated intestinal fluid to a concentration of 1 wt %. Each test consisted of 2 hours in the gastric fluid and 4 hours in the intestinal fluid, followed by exposure to the colonic fluid. The results are shown in Table 3.

TABLE 3

In vitro, disintegration test of soft capsules made of gelatin/pectinate compositions.

| Soft capsules obtained in | Gastric fluid | Intestinal fluid | Colonic fluid |
| --- | --- | --- | --- |
| Example 16a | n.d. | n.d. | disintegrates in 3 hr |
| Example 16b | n.d. | n.d. | disintegrates in 6 hr |
| Example 17a | n.d. | n.d. | disintegrates in 2 hr |
| Example 17b | n.d. | n.d. | disintegrates in 4 hr | n.d. = no disintegration

EXAMPLE 19

Preparation of soft capsule containing the drug

The air-filled soft capsules obtained in Example 14 were cut open, and 5 mg of budesonide dispersed in a peanut oil was charged into each capsule and sealed using heated pincers. The budesonide capsules thus prepared were treated with 5 wt % formaldehyde/ethanol for 10 min., dried, soaked in a 10 wt % $CaCl_2$ solution for 2 hours, washed with water and dried at a relative humidity of 20% for 48 hours to obtain an aldehyde-crosslinked gelatin/calcium pectinate capsules containing budesonide.

Comparative Example 4

Preparation of gelatin capsules containing the drug

Air-filled gelatin capsules were opened, and 5 mg of budesonide dispersed in a peanut oil was charged into each capsule sealed.

EXAMPLE 20

In vitro drug release test

The budesonide capsules obtained in Example 19 and Comparative Example 4 were subjected to in vitro drug release tests in accordance with USP 23; 2 hours in Solution 1 (pH 1.2), 4 hours in Solution 2 (pH 6.8) and a period of time in Solution 3 (as described above) sufficient for complete release of the drug. The amount of released drug was analyzed by the procedure in Example 11.

Figure 4:
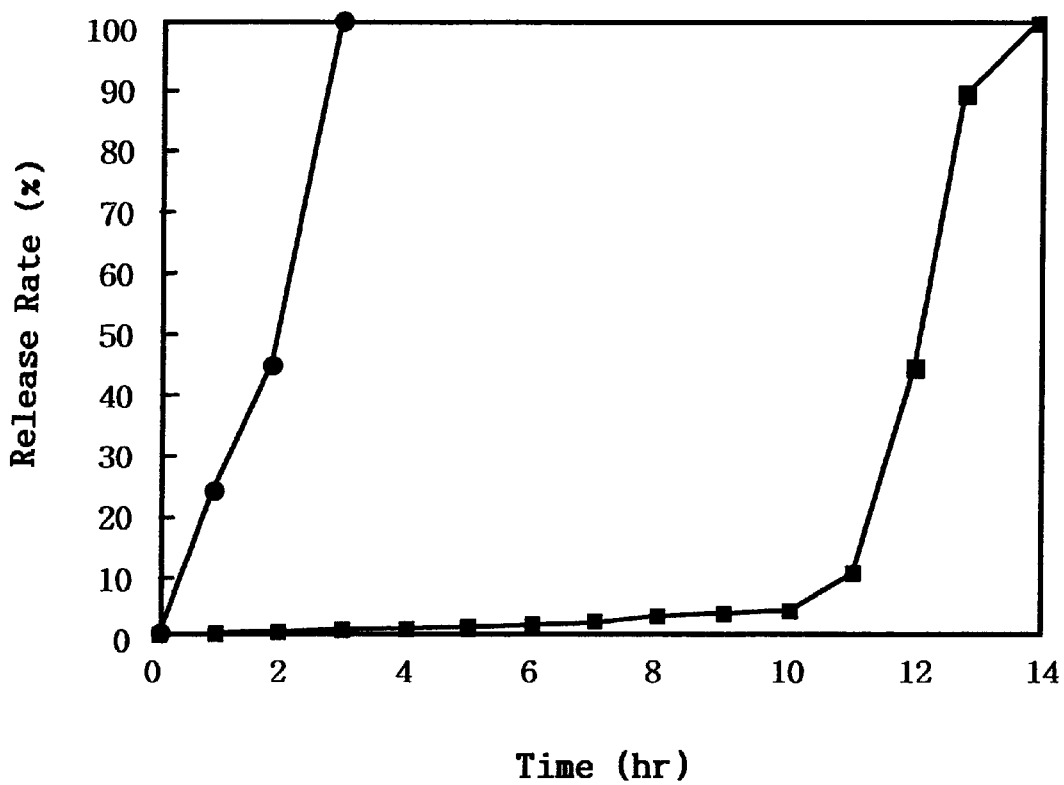
FIG. 4 exhibits the result of in vitro drug release tests conducted for a gelatin/pectinate soft capsule filled with budesonide, prepared in accordance with the present invention, and for a gelatin soft capsule.

The results are shown in FIG. 4. In FIG. 4, ■ represents a gelatin/pectinate soft capsule filled with budesonide and ♦ represents a gelatin soft capsule filled with budesonide. FIG. 4 demonstrates that the budesonide capsule obtained in Example 19 is colon specific.

EXAMPLE 21

Coating of immunoglobulin pellets

White corn starch was dissolved in an aqueous 7 wt % hydroxypropyl cellulose solution to a concentration of 5 wt %, horse immunoglobulin was added thereto and the resulting material was shaped into a pellet using CF-Granulator (CF360, Freund Ind., Japan). The pellet was coated with the coating composition as employed in Example 7 using CF-Granulator under the conditions of: coating solution feed rate=5 ml/min, inlet temperature=55° C., outlet temperature=38° C., spray air pressure=0.8 MPa and air feed rate=1.5 liter/min. The amount of the coating material in the finished pellets was estimated at 30 mg/cm².

As described above, the delivery or pharmaceutical composition of the present invention which comprises gelatin and a polysaccharide is not degraded or disintegrated in the upper gastrointestinal tract, but degraded effectively in the colon by colonic enzymes, thereby rendering the active substance contained in the composition to be delivered to the colon selectively.

The composition of the present invention may control the drug targeting site in the colon by way of using an additional component which is capable of crosslinking with gelatin or the polysaccharide and, optionally, by adding an additional colon degradable polysaccharide. Accordingly, the composition of the present invention dose not depend on the transit time and the pH of the upper gastrointestinal tract.

While the invention has been described with respect to the specific embodiments, it should be recognized that various modifications and changes may be made by those skilled in the art to the invention which also fall within the scope of the invention as defined by the appended claims.

What is claimed is:

1. A colon selective drug delivery composition comprising a pharmaceutical matrix of a complex of gelatin and an anionic polysaccharide which is degradable by a colonic enzyme.

2. The composition of claim 1 wherein the polysaccharide is selected from the group consisting of a water soluble pectinate, pectate, alginate, chondroitin sulfate, polygalacturonic acid, tragacanth gum, and a mixture thereof.

3. The composition of claim 1 wherein the composition further comprises a polyvalent metal ion.

4. The composition of claim 3 wherein the polyvalent metal ion is selected from the group consisting of a calcium ion, a magnesium ion, a strontium ion, a barium ion, a ferrous or ferric ion, a zinc ion, an aluminum ion, a bismuth ion, a zirconium ion, and a mixture thereof.

5. The composition of claim 1, or 3 wherein the composition further comprises an additional polysaccharide.

6. The composition of claim 5 wherein the additional polysaccharide is selected from the group consisting of dextran, amylose, arabinogalactan, arabinoxylan, cellulose, guar gum, laminarin, locust bean gum, pectin, starch, xylan, and a mixture thereof.

7. A colon selective pharmaceutical composition which comprises a colon selective drug delivery composition comprising a pharmaceutical matrix of a complex of gelatin and an anionic polysaccharide which is degradable by a colonic enzyme, and one or more biologically active substances.

8. The pharmaceutical composition of claim 7 wherein the delivery composition further comprises a polyvalent metal ion.

9. The pharmaceutical composition of claim 7, or 8 wherein the delivery composition further comprises an additional polysaccharide.

10. The pharmaceutical composition of claim 7, or 8 wherein the active substance is in the form of a tablet, a pill, a seed or a capsule formulation and is coated with the delivery composition to form a coated formulation.

11. The pharmaceutical composition of claim 9 wherein the active substance is in the form of a tablet, a pill, a seed or a capsule formulation and is coated with the delivery composition to form a coated formulation.

12. The pharmaceutical composition of claim 7, or 8 wherein the active substance is filled into a capsule made of the drug delivery composition.

13. The pharmaceutical composition of claim 9 wherein the active substance is filled into a capsule made of the active substance delivery composition.

* * * * *